(12) United States Patent
Owens et al.

(10) Patent No.: US 9,840,688 B2
(45) Date of Patent: Dec. 12, 2017

(54) BIOREACTOR CHAMBER

(71) Applicant: TA INSTRUMENTS-WATERS L.L.C., Milford, MA (US)

(72) Inventors: Aaron M. Owens, Plymouth, MN (US); Stefanie Vawn Biechler, Minneapolis, MN (US); David Louis Dingmann, St. Paul, MN (US); Charles W. Groepper, Waconia, MN (US); Tomas M. Hays, Blaine, MN (US); Chrysanthi Williams, Minnetonka, MN (US)

(73) Assignee: TA INSTRUMENTS-WATERS L.L.C., Milford, MA (US)

( * ) Notice: Subject to any disclaimer, the term of this patent is extended or adjusted under 35 U.S.C. 154(b) by 523 days.

(21) Appl. No.: 14/277,216

(22) Filed: May 14, 2014

(65) Prior Publication Data
US 2015/0329816 A1 Nov. 19, 2015

(51) Int. Cl.
*C12M 3/00* (2006.01)
*C12M 1/00* (2006.01)
*C12M 1/12* (2006.01)

(52) U.S. Cl.
CPC ............ *C12M 23/46* (2013.01); *C12M 23/04* (2013.01); *C12M 23/38* (2013.01); *C12M 23/50* (2013.01)

(58) Field of Classification Search
CPC ...... C12M 23/32; C12M 23/42; C12M 23/44; C12M 23/38; C12M 23/46; C12M 23/50
See application file for complete search history.

(56) References Cited

U.S. PATENT DOCUMENTS

| 7,846,715 B2 | 12/2010 | Owens et al. |
| 2007/0212750 A1* | 9/2007 | Kieffer .................. C12M 23/26 435/34 |

* cited by examiner

*Primary Examiner* — Nathan Bowers
*Assistant Examiner* — Lydia Edwards
(74) *Attorney, Agent, or Firm* — Womble Bond Dickinson (US) LLP; Deborah M. Vernon; Heath T. Misley

(57) ABSTRACT

A bioreactor system includes a sample chamber capable of receiving a specimen and a cover which can be placed on the chamber to enclose the specimen within the chamber. A first member is movable between (i) a closed position in which the member restricts the cover from being moved away from the chamber in a first direction, and (ii) an open position in which the member does not restrict the cover from being moved away from the chamber. When the first member is in the closed position there is a substantially liquid proof seal between the cover and the chamber.

22 Claims, 9 Drawing Sheets

BIOREACTOR CHAMBER

BACKGROUND

This disclosure relates to a sample chamber for containing a biomaterial.

In FIG. 1 of U.S. Pat. No. 7,846,715 (the '715 patent) a sample chamber 100 is disclosed which allows various types of tissues and other types of biomaterials to be conditioned. The contents of the '715 patent are incorporated herein by reference. A user-defined conditioning profile specifies a desired mechanical stimulation of a sample. To allow for the introduction of fluids (or other content), the sample chamber 100 is sealed to define a chamber volume 102 within which a specimen 104 is positioned. The sample chamber 100 includes two push rods 106, 108 that allow the specimen 104 to be held along an axis. Along with assisting with mechanical stimulation, the orientation and position of the push rods 106, 108 may be manually changed for adjusting the specimen.

The sample chamber 100 also includes a chamber window 114 that allows the chamber volume 102 and the specimen 104 to be viewed during conditioning. Various types of transparent material (e.g., plastics, glass, etc.) may be used to produce the window 114 while still providing the appropriate structural integrity needed for conditioning with the sample chamber 100. The window 114 is secured against a compliant element (e.g. an O-ring) with six fasteners (see FIGS. 4b and 5) in order to provide a leak-proof seal between the chamber 100 and the window 114. These fasteners (e.g. screws) apply compression around the perimeter of the sealing area. If there isn't enough compression all along the element, the seal will leak. The number and placement of the fasteners is determined by the pressure and stiffness of the elements involved.

As the fasteners and a tool used to adjust the fasteners (e.g. a hex key) are not typically attached to the chamber, they can become lost. In addition, having to tighten a number of fasteners increases the time it takes to assemble the chamber. The samples used in the chamber often contain living cells that are very sensitive to environmental changes (e.g. exposure to air flow can kill them). As such, all interactions with the chamber take place in controlled environments with filtered air. The temperature is also critical. If the cells are allowed to get too cold or too hot, they will die. This temperature window is relatively small (e.g. around 2° C.). The speed with which cellular samples can be installed in the chamber minimizes the biological stress they experience. Thus securing and sealing the chamber quickly is very advantageous. Further, the use of fasteners and related tools can introduce contamination into the chamber in which case samples will need to be discarded. It also takes additional time to clean and sterilize the fasteners and tools.

SUMMARY

All examples and features mentioned below can be combined in any technically possible way.

In one aspect, a bioreactor system includes a sample chamber capable of receiving a specimen and a cover which can be placed on the chamber to enclose the specimen within the chamber. A first member is movable between (i) a closed position in which the member restricts the cover from being moved away from the chamber in a first direction, and (ii) an open position in which the member does not restrict the cover from being moved away from the chamber. When the first member is in the closed position there is a substantially liquid proof seal between the cover and the chamber.

Embodiments may include one of the following features, or any combination thereof. The member is rotatable about an axis which is substantially parallel with a longest dimension of the chamber. The member is secured to the chamber. The member engages a portion of the cover along a first side of the cover when the member is in the closed position. The chamber includes a lip which engages a portion of the cover along a second side of the cover which is substantially opposite to the first side of the cover and restricts the cover from being moved away from the chamber in the first direction. The first side of the cover overhangs the chamber. Internal pressure in the chamber forces the member towards the closed position. The chamber includes a lip which engages a portion of the cover along a side of the cover. The chamber includes at least one protrusion at both ends of the chamber which positions the cover in a second direction. The cover includes a groove in which a portion of the member resides when the member is in the closed position. The member can be removed from the chamber when the member is in the open position. The member is rotatable about an axis which is substantially perpendicular with a longest dimension of the chamber. The bioreactor system further includes a second member which is movable between (i) a closed position in which the second member restricts the cover from being moved away from the chamber in the first direction, and (ii) an open position in which the second member does not restrict the cover from being moved away from the chamber. The first and second members engage the cover at respective opposite ends of the cover. The member is an elongated member.

In another aspect, a bioreactor system includes a sample chamber capable of receiving a specimen and a cover which can be placed on the chamber to enclose the specimen within the chamber. The chamber includes a lip which engages a portion of the cover along a first side of the cover to resist the cover in moving in at least a first direction.

Embodiments may include one of the above and/or below features, or any combination thereof. The bioreactor system further includes a compressible sealing member which can be compressed between the cover and the chamber to provide a substantially leak proof seal. The bioreactor system further includes a member which is movable between (i) a closed position in which the member restricts the cover from being moved away from the chamber, and (ii) an open position in which the member does not restrict the cover from being moved away from the chamber. The member engages a portion of the cover along a second side of the cover. The second side of the cover is substantially opposite to the first side of the cover. The lip includes a transition zone surface which guides the cover when the cover is first inserted into the chamber and a retaining surface which assists in securing the cover to the chamber once the cover is fully inserted into the chamber.

In another aspect, a bioreactor system includes a sample chamber capable of receiving a specimen and a cover which can be placed on the chamber to enclose the specimen within the chamber. The chamber includes at least one protrusion at both ends of the chamber which positions the cover in a first direction.

Embodiments may include one of the above and/or below features, or any combination thereof. The member engages at least a substantial portion of the cover along a side of the cover. The bioreactor system further includes a lip which engages at least a portion of the cover along a side of the cover to resist the cover in moving in at least one direction.

In another aspect, a bioreactor system includes a sample chamber capable of receiving a specimen. A fluid reservoir container is secured to the chamber. Fluid can be supplied from the reservoir to the chamber. The container is able to receive fluid which is exhausted from the chamber.

Embodiments may include one of the above and/or below features, or any combination thereof. The bioreactor system further includes a cover which can be placed on the container and a first member which is movable between (i) a closed position in which the member restricts the cover from being moved away from the container, and (ii) an open position in which the member does not restrict the cover from being moved away from the chamber. The first member is elongated. The container includes at least one protrusion at both ends of the container which positions the cover in a certain direction. The container includes a lip which engages a portion of the cover along a side of the cover. The chamber and container are a unitary structure. The container includes a port which allows liquid to be inserted into the container. The container is positionable in (i) a first position in which a long axis of the container is substantially vertical, and (ii) a second position in which the long axis of the container is substantially horizontal, the port being located and oriented so that the container can be substantially filled with liquid via the port when the container is positioned in either of the first and second positions.

In another aspect, a bioreactor system includes one of a sample chamber capable of receiving a specimen and a container for holding a fluid. The one of the sample chamber and container having a channel for receiving a sealing member which can be engaged with a cover to provide a substantially fluid tight seal. The channel has a plurality of pinch features which are each a necked down portion of the channel that reduces the diameter of the sealing member across the channel and assists in retaining the sealing member in the channel.

In another aspect, a bioreactor system includes a sample chamber capable of receiving a specimen and a cover which can be placed on the chamber to enclose the specimen within the chamber. The chamber includes a port which allows liquid to be inserted into the chamber. The chamber is placeable in (i) a first position in which a long axis of the chamber is substantially vertical, and (ii) a second position in which the long axis of the chamber is substantially horizontal, the port being located and oriented so that the chamber can be substantially filled with liquid via the port when the chamber is positioned in either of the first and second positions.

Embodiments may include one of the above and/or below features, or any combination thereof. The chamber is placeable in a third position in which the long axis of the chamber is substantially horizontal and the chamber has been rotated about ninety degrees about the long axis from the second position. When the chamber is in the third position the chamber can be substantially filled with liquid via an opening in the chamber that is exposed when the cover is removed from the chamber.

DETAILED DESCRIPTION

The description below describes various versions of a bioreactor system having a bioreactor sample chamber that can receive a specimen. A cover, preferably transparent, can be placed on the chamber to enclose the specimen within the chamber. This cover allows viewing of the specimen and measurements of the specimen to be taken. An elongated member is movable between a closed position in which the member restricts the cover from being moved away from the chamber and an open position in which the member does not restrict the cover from being moved away from the chamber. This arrangement allows the cover to be quickly sealed to or removed from the chamber with no tools and no fasteners (both of which can become contaminated or lost) in a simple, intuitive manner.

Figure 1:
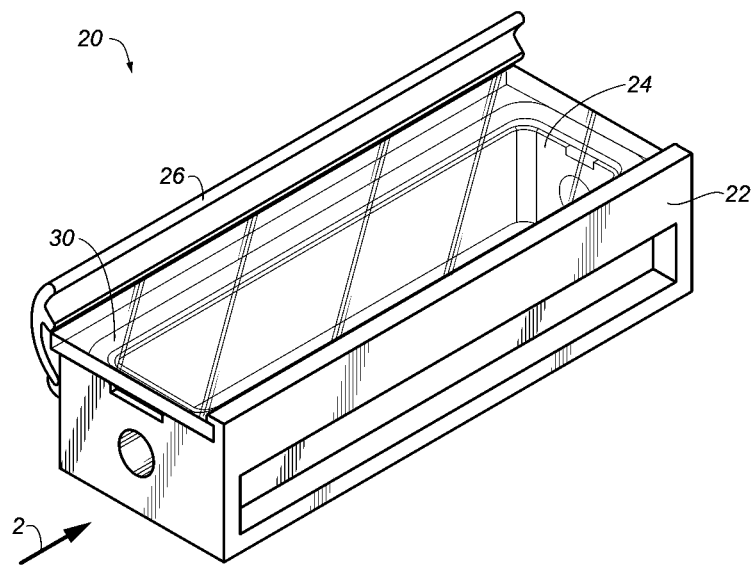
FIG. 1 is a perspective view of a chamber of a bioreactor system capable of receiving a specimen.
Figure 2:
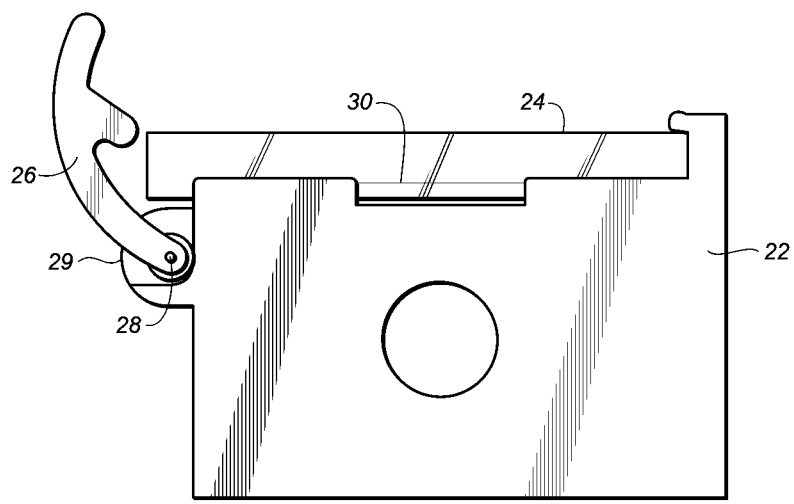
FIG. 2 is an end view of the chamber of a bioreactor system of FIG. 1 taken along the direction 2 with an elongated member in an open position.

Referring to FIGS. 1 and 2, a bioreactor system 20 includes a plastic bioreactor sample chamber 22 that is capable of receiving a specimen (e.g. a biomaterial, not shown). The specimen may be a biologic material, a synthetic material, or a combination of a biologic material and a synthetic material. Examples of a biologic material include native tissue, processed tissue, cell-seeded biomaterial scaffolds, and tissue-engineered constructs. Examples of a synthetic material include medical devices and acellular biomaterials and scaffolds.

In order to place a specimen inside the chamber, a cover 24, preferably transparent, is removed from the chamber 22, the specimen is placed inside the chamber, and then the cover is placed back on the chamber to enclose the specimen within the chamber. Although the cover 24 in this example is substantially flat, the cover may have other shapes (e.g. curved). The sample is held within the chamber along an axis as described above in the background section. An elongated member 26 is shown in an open position in which the member does not restrict the cover 24 from being moved away from the chamber 22. The elongated member 26 can be replaced by two or more shorter members. The member 26 can be rotated about an axis and is secured to the chamber 22 by pivoting features 28. The pivoting features 28 include an internal surface which is substantially co-linear with the axis. The pivoting features 28 reside in an external housing surface 29. The axis is substantially parallel with a longest dimension of the chamber 22 A compressible sealing member in the form of an O-ring 30 is located between the cover 24 and other covers of the chamber when the cover 24 is placed on the chamber. The chamber 22, cover 24 and member 26 can be used as a standalone unit, or they can be part of a larger system that includes, for example, pumps and filters.

Figure 3:
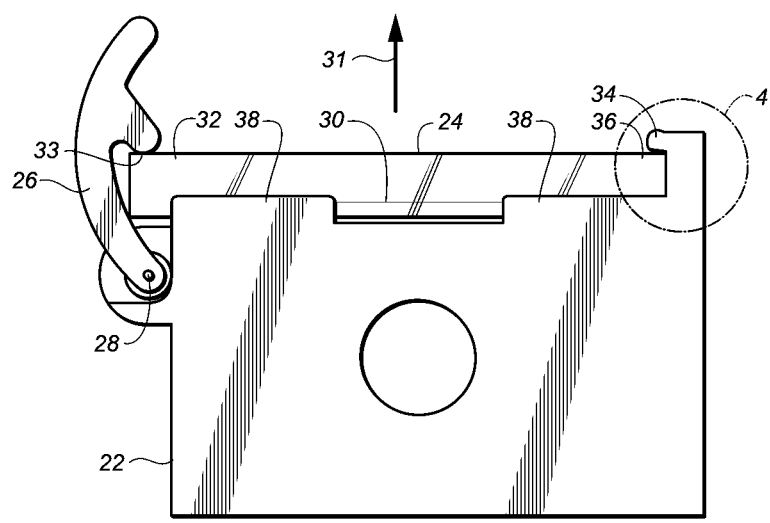
FIG. 3 is an end view of the chamber of a bioreactor system of FIG. 1 taken along the direction 2 with the elongated member in a closed position.

With reference to FIG. 3, the movable member 26 has been rotated from the open position (FIG. 1) to a closed position in which the member restricts the cover 24 from being moved away from the chamber 22 in a direction 31. The O-ring 30 is compressed between the cover 24 and the chamber 22 to provide a substantially leak proof seal against fluids exiting the chamber. In the closed position the elongated member 26 engages a portion of the cover 24 along a first side 32 of the cover. In this example the cover 24 extends outward at the first side 32 to overhang the chamber 22. The contact location 33 between the side 32 of the cover 24 and the member 26 is positioned outside of the pivoting features 28. This creates a small moment arm about the axis of rotation for the member 26. When the chamber 22 is pressurized with fluid, a force on the member 26 generates a moment that causes the member 26 to rotate towards the chamber 22. This arrangement locks the member 26 from moving from the closed position to the open position.

Figure 4:
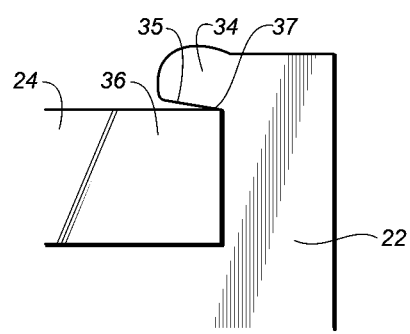
FIG. 4 is a close up view of a portion 4 of FIG. 3.
Figure 5:
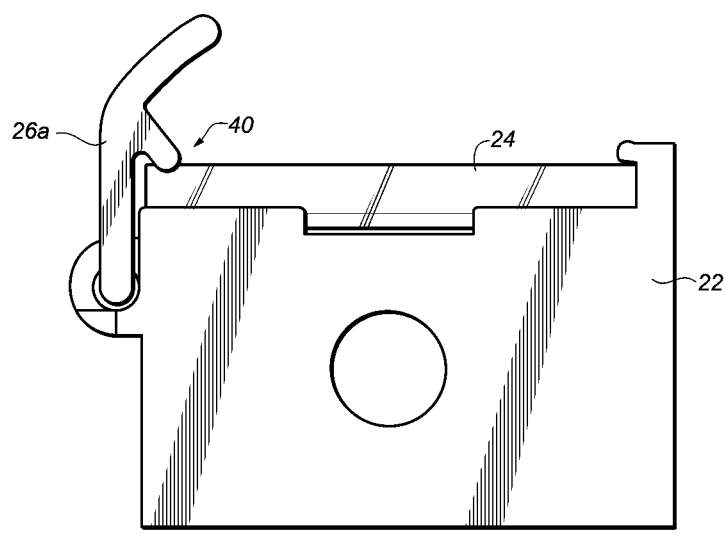
FIG. 5 is an end view of another example of a chamber of a bioreactor system with a different version of an elongated member in a closed position.

Referring to FIGS. 3 and 4, the chamber 22 includes a lip 34 which engages at least a portion of the cover 24 along a second side 36 of the cover which is substantially opposite to the first side of the cover 32. The lip 34 restricts the cover 24 from being moved away from the chamber 22 in the first direction 31. The chamber includes at least one protrusion 38 at both ends of the chamber (see FIG. 1, in this example there are two protrusions at each end) which positions the cover 24 in a second direction (this direction is in and out of the sheet on which FIG. 3 resides) which is substantially perpendicular to the first direction 31. The lip 34 includes a transition zone surface 35 leading into a retaining surface 37 of a constrained zone. After the cover 24 is inserted into the transition zone surface 35 at an angle and then up against the retaining surface 37, the cover 24 is compressed into a flat orientation by the member 26. The transition zone surface 35 guides the cover 24 when the cover is first inserted into the chamber 22, and then the retaining surface 37 assists in securing the cover to the chamber once the cover is fully inserted into the chamber. This arrangement provides for the proper compression on the O-ring 30. The geometries are designed to allow for the cover 24 to articulate through the transition zone surface 35 into the retaining surface 37 of the constrained zone FIG. 5 shows another example of the bioreactor system in which a contoured groove 40 is provided in the cover 24 to allow the hinged elongated member 26a to toggle over the cover edge and reside in the groove. When the chamber 22 is pressurized, the groove 40 locks the member 26a from moving from the closed position to the open position under pressure.

Figure 6:
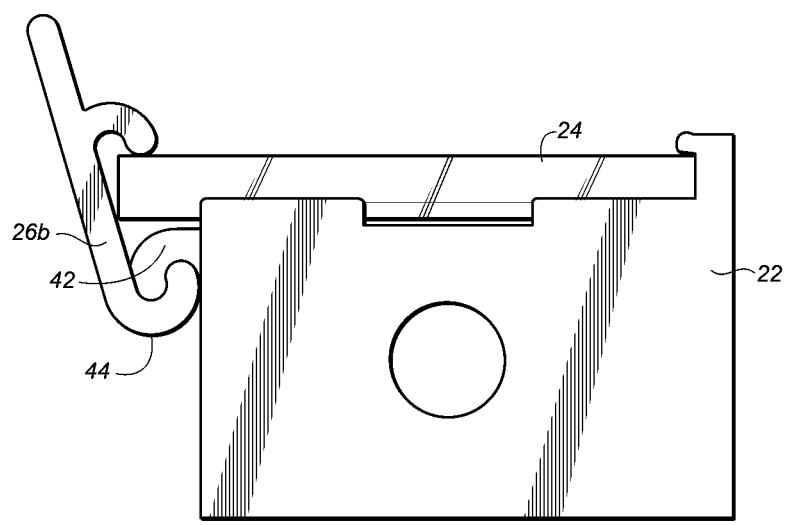
FIG. 6 is an end view of another example of a chamber of a bioreactor system with a different version of an elongated member in a closed position.

FIG. 6 shows another example of a bioreactor system in which an elongated member 26b is arranged in an overturning moment configuration. Positive pressure inside the chamber pushing up on the cover 24 will bias the member 26b in a clockwise direction. That is, the member 26b is forced to rotate towards the chamber due to the geometry of the arrangement. This results in the member 26 b remaining in the closed position during times of positive pressure inside the chamber. The member 26b is retained to the chamber 22 by a curved locking extension 42 which engages with a mating curved portion 44 of the member 26b. The member 26b can be completely separated from the chamber 22 after the member 26b is moved to the open position.

Figure 7:
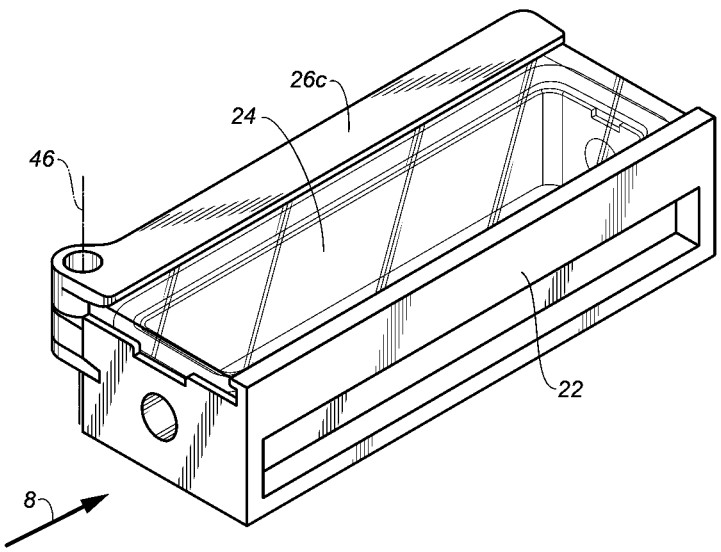
FIG. 7 is a perspective view of another example of a chamber of a bioreactor system with a different version of an elongated member in a closed position.
Figure 8:
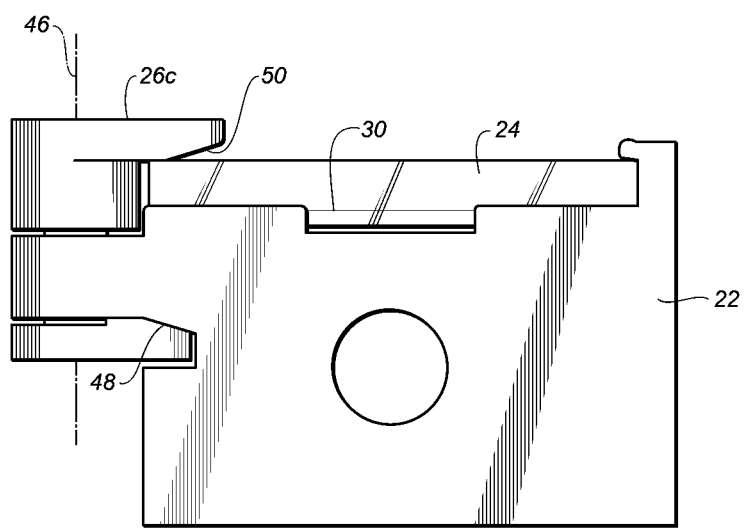
FIG. 8 is an end view of the chamber of a bioreactor system of FIG. 7 taken along the direction 8.

Turning to FIG. 7, another example of a bioreactor system is shown in which an elongated member 26c can be rotated about an axis 46 which is substantially perpendicular to a longest dimension of the chamber 22. The cover 24 is retained between two opposing cam surfaces 48 and 50 built into this member 26c. The compression of the O-ring 30 is set by the distance between the surfaces 48 and 50. A locking of member 26C is inherent in this example as a force required to open and close the member is perpendicular to forces generated from internal pressure in the chamber 22 which would urge the cover 24 in a direction parallel with the axis 46.

Figure 9:
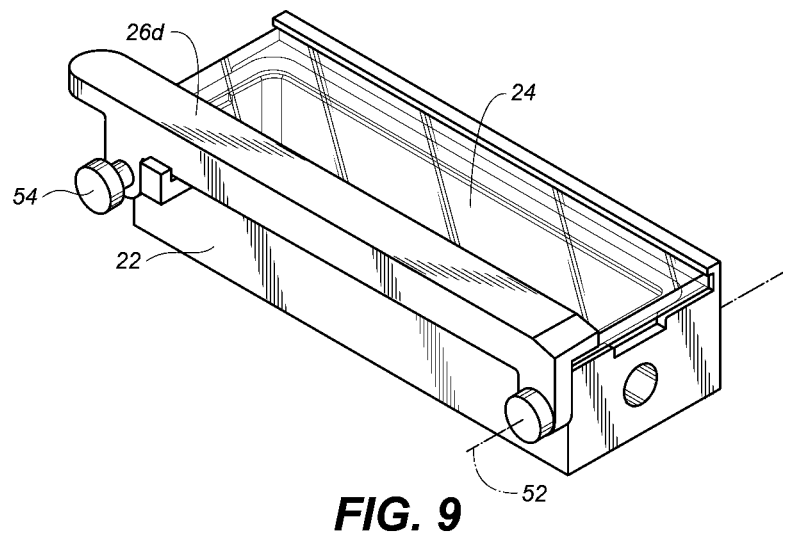
FIG. 9 is a perspective view of another example of a chamber of a bioreactor system with a different version of an elongated member in a closed position.
Figure 10:
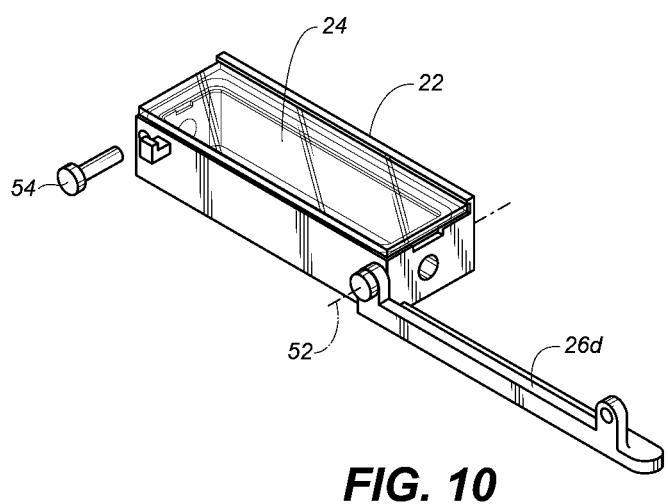
FIG. 10 is a perspective view of the chamber of a bioreactor system of FIG. 9 with the elongated member in an open position.

Referring to FIGS. 9 and 10, another example of a bioreactor system in which an elongated member 26d can be rotated about an axis 52 which is substantially perpendicular to a longest dimension of the chamber 22. In FIG. 9 the member 26d is shown in the closed position with a locking pin 54 securing the member in the this position. The pin 54 engages the member 26d towards an end of the member which is opposite to an end of the member which rotates about the axis 52. In FIG. 10 the pin 54 has been removed and the member 26d has been rotated to an open position. Now the cover 24 can be removed from the chamber 22 if desired. Pressure forces from inside the chamber are reacted by the pin 54 holding the member 26d in the closed position.

Figure 11:
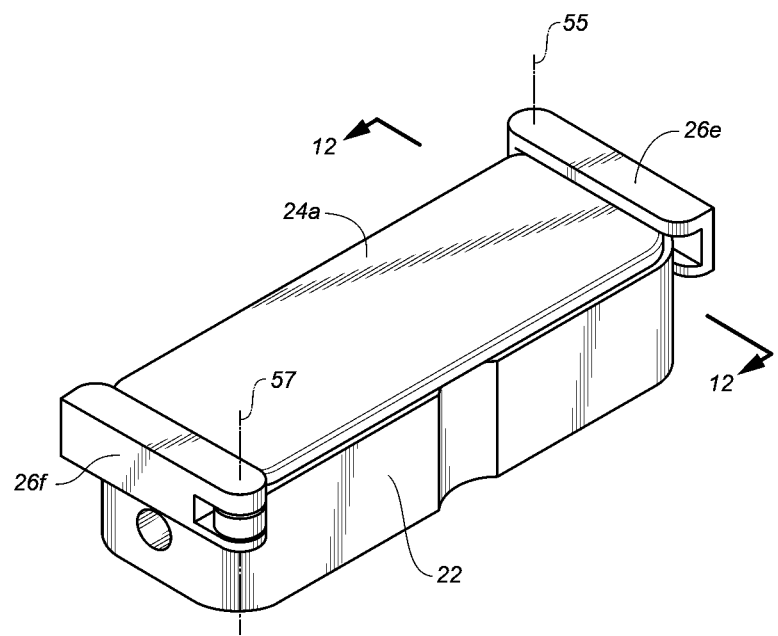
FIG. 11 is a perspective view of another example of a chamber of a bioreactor system with a pair of elongated members in closed positions.
Figure 12:
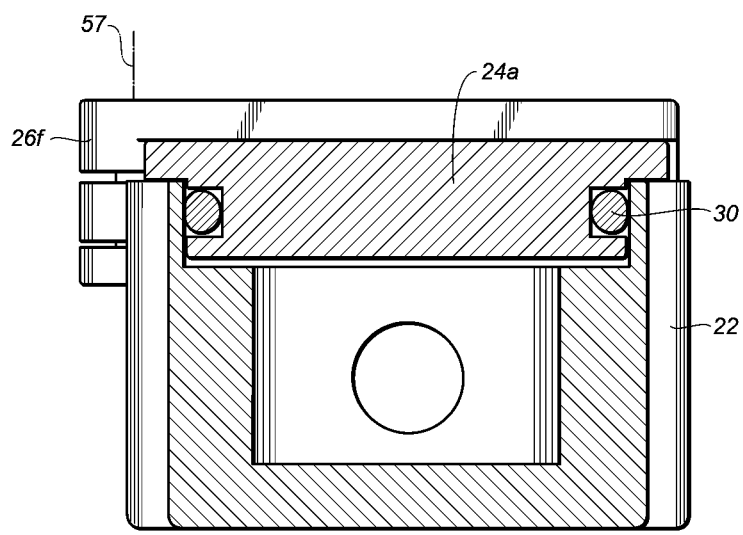
FIG. 12 is a sectional view of FIG. 11 taken along lines 12-12 which shows elongated members in a closed position.

Turning now to FIGS. 11 and 12, a pair of elongated members 26e and 26f are each rotatably secured to the chamber 22 at respective opposite ends of the chamber. The members 26e and 26f rotate about respective axes 55 and 57. The O-ring 30 in this example is located in a channel that extends along a radial portion of a cover 24a. In operation, the members 26e and 26f are rotated to open positions, the cover 24a is pressed onto the chamber 22 to compress the O-ring 30 between the cover and the chamber, and then the members 26e and 26f are rotated to their respective closed positions (shown in FIG. 11) to secure the cover to the chamber. Because the O-ring 30 operates in a direction orthogonal to the axes 55 and 57, pressure inside the chamber doesn't act to alleviate the compressive retaining forces. Thus, the cover 24a simply needs to be retained, (substantial compressive forces do not need to be provided).

Figure 13:
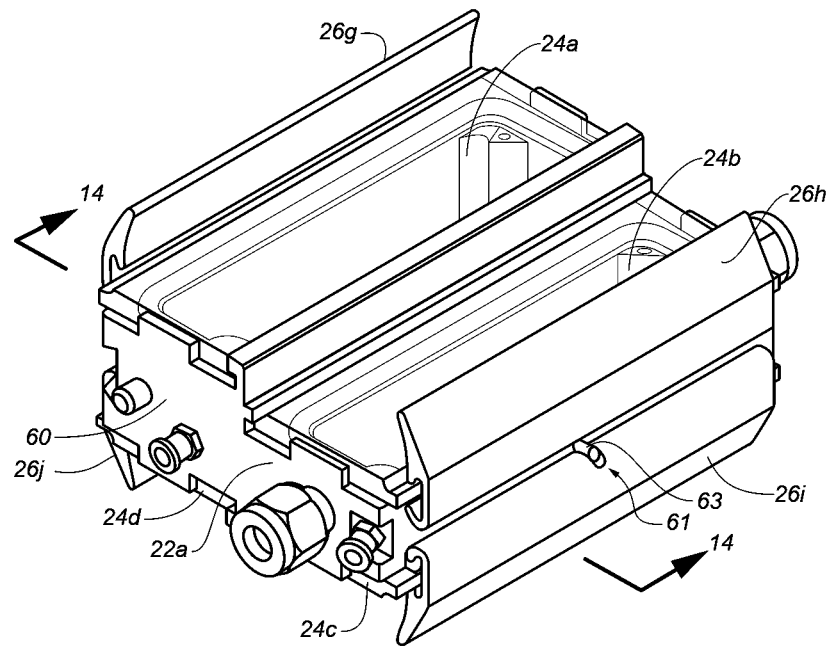
FIG. 13 is a perspective view of another example of a chamber of a bioreactor system with an integrated fluid reservoir container.
Figure 14:
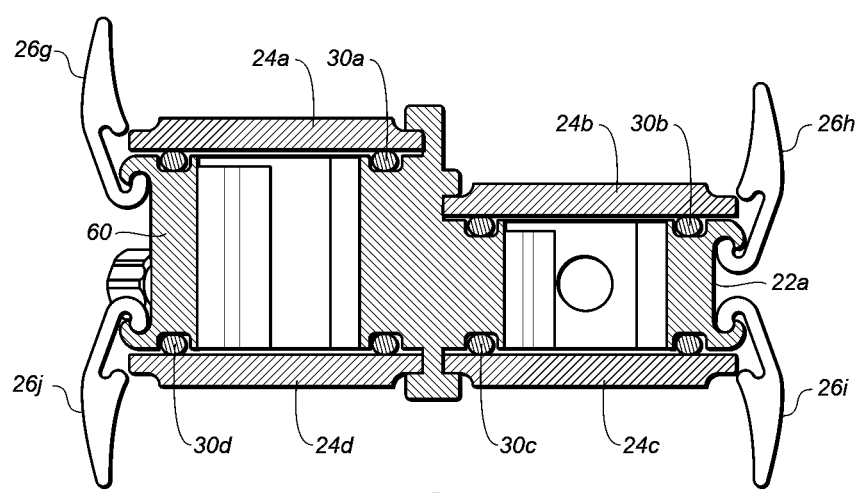
FIG. 14 is a sectional view of FIG. 13 taken along lines 14-14 which shows elongated members in an open position.

Referring to FIGS. 13 and 14, another example of a bioreactor system is shown with a sample chamber 22a capable of receiving a specimen. A fluid reservoir container 60 is secured to (e.g. a unitary structure with) the chamber 22a. If the container 60 is a separate element from the chamber 22a, they can be connected, for example, with integrated joints or snaps. Fluid can be supplied (e.g. pumped) to the chamber 22a from the container 60 through tubing (not shown). The container 60 can also receive fluid which is exhausted from the chamber 22a through tubing (not shown). The exhausted fluid may be filtered before it is returned to the container 60. Alternatively, the exhausted fluid can be moved through tubing (not shown) to a waste fluid container (not shown).

Four covers 24a-d are used to close up both the chamber 22a and the container 60. Each of the four covers 24a-d can be placed on a side of chamber 22a or the container 60. Similar to FIG. 6, a series of four elongated members 26g-j are each movable between (i) a closed position in which a member restricts a respective cover from being moved away from the chamber 22a or the container 60, and (ii) an open position in which a member does not restrict a respective cover from being moved away from the chamber or container. The member 26i has a cutout 61 which accommodates a pin 63 that is secured to the chamber 22a. Each of the other three members 26g, h and j has a similar arrangement. The pin 63 allows the member 26i to move between its closed and open positions while preventing the member 26i from being removed from the chamber 22a (unlike in FIG. 6 where the elongated member 26b can be removed from the chamber 22). Four O-rings 30a-d are located adjacent to the respective covers 24a-d.

Figure 15:
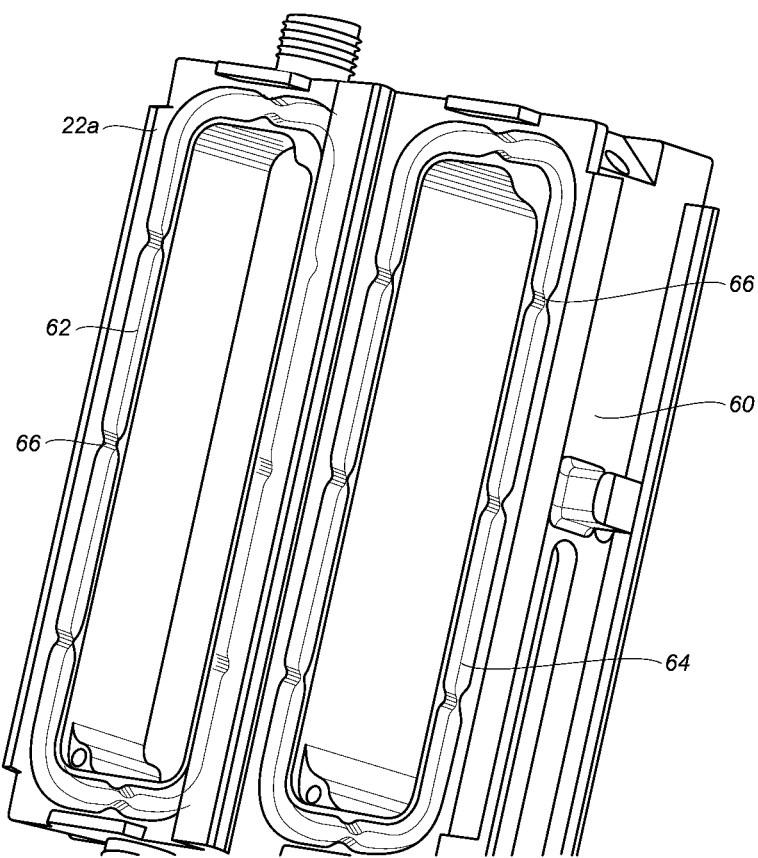
FIG. 15 is a perspective view of the chamber and reservoir of FIG. 13 with portions removed to facilitate viewing.

Turning to FIG. 15, the bioreactor system of FIG. 13 is shown from a different perspective view. The covers 24a-d, the elongated members 26g-j, and the O-rings 30a-d have been removed. Channels 62 and 64 are respectively provided in the chamber 22a and the container 60 for retaining respective O-rings 30c and 30d (see FIG. 14). There are two more channels (not visible in FIG. 15) on the opposite side of the chamber 22a and the container 60 for retaining the respective O-rings 30b and 30a. If a standard O-ring channel was used, the O-rings may become disturbed, or even dislodged, when the doors 24a-d are installed or removed to/from the chamber 22a and the container 60. These issues can be a source of lost time during specimen installation.

In order to expedite the assembly process of the chamber 22a and container 60, and to reduce the specimen exposure time, it is very desirable to retain the O-rings 30a-d in their respective channels. This objective is attained by using pinch features 66 in each of the channels. Each channel has a periodic necked down portion which results in, for example, about a 10% diametric O-ring pinch across the channel. Each channel has eight pinch features 66 equally spaced around the channel to retain the O-ring in the channel. Each O-ring in this example preferably has a diameter of about 0.139 inches. The pinch features 66 each contact the O-ring with a contact patch that is relatively small compared to the compression of the O-ring, and have large lead in and lead out radii to facilitate the cleaning and sterilization process. The size and spacing of the pinch features has been selected to generate adequate holding force, but not interfere with the normal O-ring sealing compression mechanism.

Figure 16:
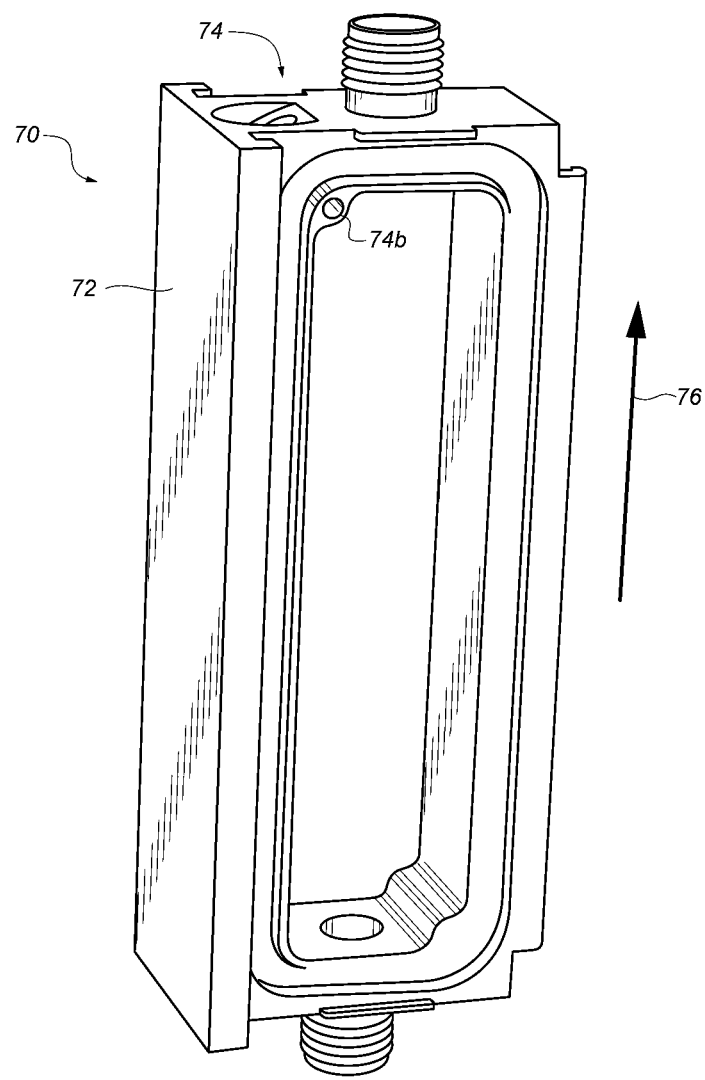
FIG. 16 is another example of a chamber of a bioreactor system which can contain a specimen.

Referring to FIG. 16, another example of a bioreactor system 70 includes a sample chamber 72 capable of receiving a specimen (not shown). As described above relative to FIG. 14, a pair of covers (not shown) can be placed on the chamber 72 to enclose the specimen within the chamber. The chamber 72 includes a port 74 which allows liquid to be inserted into the chamber through an end of the port 74b when the two covers are secured to the chamber with a specimen in the chamber. The chamber 72 can be placed in (i) a first position in which a long axis 76 of the chamber is substantially vertical (as shown in FIG. 16), and (ii) a second position in which the long axis 76 of the chamber is substantially horizontal (the chamber 72 in FIG. 16 would be rotated about 90 degrees clockwise). The port 74 including the port end 74b is located and oriented so that the chamber 72 can be substantially filled with liquid via the port when the chamber is positioned in either of the first and second positions. This arrangement of the port can also be applied to the container 60 (FIG. 13). The chamber 72 can also be placed in a third position in which the long axis 76 of the chamber is substantially horizontal and the chamber has been rotated about ninety degrees about the long axis from the second position. When the chamber 72 is in the third position the chamber can be substantially filled with liquid via an opening in the chamber that is exposed when the cover is removed from the chamber.

A number of implementations have been described. Nevertheless, it will be understood that additional modifications may be made without departing from the scope of the inventive concepts described herein, and, accordingly, other embodiments are within the scope of the following claims. For example, instead of rotatably securing the elongated member to the chamber 22, the member could instead be secured (e.g. rotatably) to the cover 24.

What is claimed is:

1. A bioreactor system, comprising:
   a sample chamber capable of receiving a specimen;
   a cover which can be placed on the chamber to enclose the specimen within the chamber, the cover including a first side and a second side substantially opposite to the first side;
   a first member which is movable between (i) a closed position in which the member restricts the cover from being moved away from the chamber in the first direction, and (ii) an open position in which the member does not restrict the cover from being moved away from the chamber, whereby when the first member is in the closed position there is a substantially liquid proof seal between the cover and the chamber, the first member configured to engage a portion of the cover along the first side of the cover when the first member is in the closed position; and
   a lip extending from a portion of the sample chamber and configured to engage a portion of the cover along the second side of the cover and restrict the cover from being moved away from the chamber in a first direction.

2. The bioreactor system of claim 1, wherein the member is secured to the chamber.

3. The bioreactor system of claim 1, wherein the member is rotatable about an axis, and wherein the first side of the cover overhangs the chamber, whereby the internal pressure in the chamber forces the member towards the closed position.

4. The bioreactor system of claim 1, wherein the chamber includes at least one protrusion at both ends of the chamber which positions the cover in a second direction.

5. The bioreactor system of claim 1, wherein the cover includes a groove in which a portion of the first member resides when the first member is in the closed position.

6. The bioreactor system of claim 1, wherein the member can be removed from the chamber when the member is in the open position.

7. The bioreactor system of claim 1, wherein the member is rotatable about an axis which is substantially perpendicular with the longest dimension of the chamber.

8. The bioreactor system of claim 1, wherein the member is an elongated member.

9. The bioreactor system of claim 1, wherein the member is rotatable about an axis which is substantially parallel with a longest dimension of the chamber.

10. A bioreactor system, comprising:
a sample chamber capable of receiving a specimen; and
a cover which can be placed on the chamber to enclose the specimen within the chamber, the chamber including a lip which engages a portion of the cover along a first side of the cover to resist the cover in moving in at least a first direction.

11. The bioreactor system of claim 10, further including a compressible sealing member which can be compressed between the cover and the chamber to provide a substantially leak proof seal.

12. The bioreactor system of claim 10, further including a member which is movable between (i) a closed position in which the member restricts the cover from being moved away from the chamber, and (ii) an open position in which the member does not restrict the cover from being moved away from the chamber.

13. The bioreactor system of claim 12, wherein the member is secured to the chamber.

14. The bioreactor system of claim 10, wherein the chamber includes at least one protrusion at both ends of the chamber which positions the cover in a second direction.

15. The bioreactor system of claim 10, wherein the lip includes a transition zone surface which guides the cover when the cover is first inserted into the chamber and a retaining surface which assists in securing the cover to the chamber once the cover is fully inserted into the chamber.

16. A bioreactor system, comprising:
a sample chamber capable of receiving a specimen;
a cover which can be placed on the chamber to enclose the specimen within the chamber, the chamber including at least one protrusion at both ends of the chamber which positions the cover in a first direction; and
a lip extending from a portion of the sample chamber and configured to engage at least a portion of the cover along a side of the cover to resist the cover in moving in at least one direction.

17. The bioreactor system of claim 16, further including a compressible sealing member which can be compressed between the cover and the chamber to provide a substantially leak proof seal.

18. The bioreactor system of claim 16, further including a member which is movable between (i) a closed position in which the member restricts the cover from being moved away from the chamber, and (ii) an open position in which the member does not restrict the cover from being moved away from the chamber.

19. The bioreactor system of claim 18, wherein the member is secured to the chamber.

20. The bioreactor system of claim 18, wherein the member engages at least a substantial portion of the cover along a side of the cover.

21. A bioreactor system, comprising:
a sample chamber capable of receiving a specimen;
a cover which can be placed on the chamber to close the specimen within the chamber, the chamber including a port which allows liquid to be inserted into the chamber, the chamber being placeable in (i) a first position in which a long axis of the chamber is substantially vertical, and (ii) a second position in which the long axis of the chamber is substantially horizontal, the port being located and oriented so that the chamber can be substantially filled with liquid via the port when the chamber is positioned in either of the first and second positions; and
a lip extending from a portion of the sample chamber and configured to engage at least a portion of the cover along a side of the cover to resist the cover in moving in at least one direction.

22. The bioreactor system of claim 21, wherein the chamber is placeable in a third position in which the long axis of the chamber is substantially horizontal and the chamber has been rotated about ninety degrees about the long axis from the second position, whereby when the chamber is in the third position the chamber can be substantially filled with liquid via an opening in the chamber that is exposed when the cover is removed from the chamber.

* * * * *